(12) United States Patent
Ducret et al.

(10) Patent No.: US 7,287,417 B2
(45) Date of Patent: Oct. 30, 2007

(54) DEVICE FOR DETERMINING THE WETTING OF A WALL BY A LIQUID

(75) Inventors: Philippe Ducret, Corbieres (FR); Quentin Jogand, La Notte d'Aigues (FR)

(73) Assignee: Commissariat a l'Energie Atomique (FR)

( * ) Notice: Subject to any disclaimer, the term of this patent is extended or adjusted under 35 U.S.C. 154(b) by 0 days.

(21) Appl. No.: 10/518,688

(22) PCT Filed: Jun. 24, 2003

(86) PCT No.: PCT/FR03/01943

§ 371 (c)(1),
(2), (4) Date: Oct. 25, 2005

(87) PCT Pub. No.: WO04/001368

PCT Pub. Date: Dec. 31, 2003

(65) Prior Publication Data

US 2006/0150718 A1 Jul. 13, 2006

(30) Foreign Application Priority Data

Jun. 25, 2002 (FR) .................................. 02 07848

(51) Int. Cl.
*G01N 5/02* (2006.01)
(52) U.S. Cl. ......................................... 73/73
(58) Field of Classification Search ................. 73/73, 73/649
See application file for complete search history.

(56) References Cited

U.S. PATENT DOCUMENTS 3,444,726 A * 5/1969 Pitcher et al. ............. 73/61.75

FOREIGN PATENT DOCUMENTS

| EP | 0 250 291 A1 | 6/1987 |
| EP | 0 250 291 B1 | 12/1987 |
| FR | 2 271 581 | 5/1975 |
| GB | 1123939 | 12/1966 |

OTHER PUBLICATIONS

Search report from French Patent Office citing three references: EP 0 250 291; 2 271 581; 1 123 939.
English Translation of French International Preliminary Examination Report Form PCT/IPEA/409 (5 sheets) plus Form PCT/IB/338 (1 sheet).

* cited by examiner

*Primary Examiner*—Hezron Williams
*Assistant Examiner*—Tamiko Bellamy
(74) *Attorney, Agent, or Firm*—Anderson Kill & Olick, PC

(57) ABSTRACT

Ultrasonic waves passing through guides (5, 6) are emitted towards a target (2) immersed in a liquid in order to infer the wetting of this target from certain features of the received signal. The invention is notably applied to the study of liquid heavy metals.

17 Claims, 5 Drawing Sheets

DEVICE FOR DETERMINING THE WETTING OF A WALL BY A LIQUID

The object of this invention is a device for determining the wetting of a wall by a liquid.

Certain fields of the art require that one be concerned with this issue and for example determine whether walls of tanks, piping, measurement probes or of nuclear reactor tools, are wetted with certain metals which may be sodium, potassium, lead, bismuth or their alloys. Depending on the case, wetting is essential or forbidden on the contrary.

The wetting of a solid by a liquid is a phenomenon which depends on many factors including, in addition to the chemical nature of the liquid metal and of the wall, the purity of the liquid, the state of the surface of the wall, the temperature, the nature and presence of occluded gases in the liquid and the time for putting the liquid metal in the presence of the wall. Wetting may be defined as the adhesion of the metal on the wall at an atomic scale and it is not easy to determine it directly. Different criteria and measurement methods have been contemplated for determining the wetting, its absence or an intermediate state on the walls of an object immersed in a liquid metal bath, by operating, if necessary, on a control specimen of the object.

So the idea of correlating wetting with the spreading of a drop or with the capillary rising of the liquid metal dawned upon us, without obtaining a very accurate result, because of the numerous influencing factors.

The invention belongs to a different category of methods and comprises two fundamental embodiments, but which are closely related as they are based on the transmission of ultrasonic waves through the interface of the wall and of the liquid. One of them is a device for determining the wetting of a wall by a liquid, characterized in that it comprises: a capacity for the liquid; a control object of the wall placed in the capacity; an emitter and a receiver of ultrasonic waves; and two waveguides passing through the capacity, located in extension, the emitter and the receiver being respectively mounted on ends of the waveguides extending out of the capacity, and the object being placed between the waveguides; the object having a thickness selected for favoring the passage of waves from the emitter. And the other one is a device for determining the wetting of a wall by a liquid, characterized in that it comprises: a capacity for the liquid; a control object of the wall placed in the capacity; an emitter and a receiver of ultrasonic waves; and two waveguides passing through the capacity located side-by-side, the emitter and the receiver being respectively mounted on ends of the waveguides extending out of the capacity, and the object being placed in front of the waveguides, the object having a front surface selected for favoring reflections of the waves between the waveguides.

In many tangible cases, when the investigated liquid is a molten metal, the capacity should be equipped with heating means; the waveguides will then be equipped with cooling means located outside the capacity, and which may consist of a casing surrounding each of the waveguides between the capacity and either the emitter or the receiver.

The invention will now be described in all its developments by means of the following figures.

Figure 1:
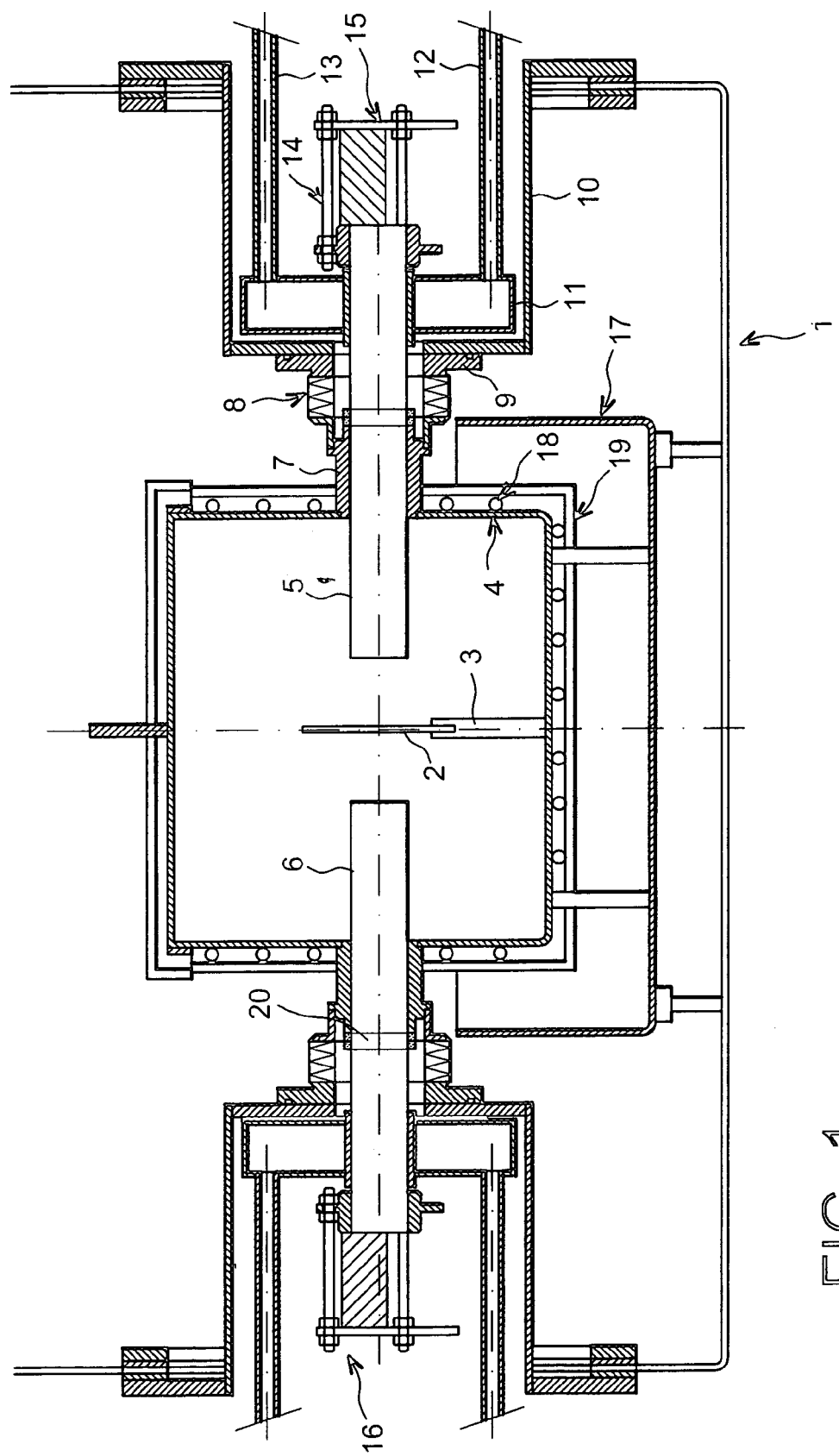
FIG. 1 is a general view of the device according to the invention.

FIG. 1 describes a first embodied device of the invention. It is formed in an enclosure 1 which allows the atmosphere with a desired composition to be blown therein and contains a target 2 which is an imitation of the wall to be investigated and which is found, supported by a support 3, in a capacity 4 included in the enclosure 1. Two waveguides 5 and 6 facing each other penetrate the capacity 4 and stop at a certain distance from the target 2. The seal of the capacity 4 is guaranteed by passageway sleeves 7 for the waveguides 5 and 6, the ends of which are soldered to the capacity 4 and to a protruding flange 20 at a section of the waveguides 5 and 6 outside the capacity 4. Bellows 8 extend the passageway sleeves 7 and extend up to brackets 9 connected to casings 10 themselves attached from the rear to the enclosure 1. The bottom of the casings 10 (near brackets 9) is occupied by water cases 11, the contents of which are renewed through inlet and outlet conduits 12 and 13. The waveguides 5 and 6 pass through the water cases 11 which are recessed in their center, and their ends are equipped with supports 14 of ultrasonic wave transducers 15 and 16, the first of which is for emitting ultrasonic waves and the second one is for receiving them. Reference number 17 overall designates a supporting structure of the capacity 4 in the enclosure 1 and reference number 18 designates means for heating the capacity 4 in order to conduct the experiment at the desired temperature. Double soldering of the passageway sleeves 17 makes the capacity 4 leak-proof, and the water cases 11 form cooling means which acts as a barrier to heat flowing through the waveguides 5 and 6 and which might have reached transducers 15 and 16. The bellows 8 covering the hot portion of the waveguides 5 and 6 protect the outside. A heat shield 19 is also positioned around capacity 4.

Figure 2A:
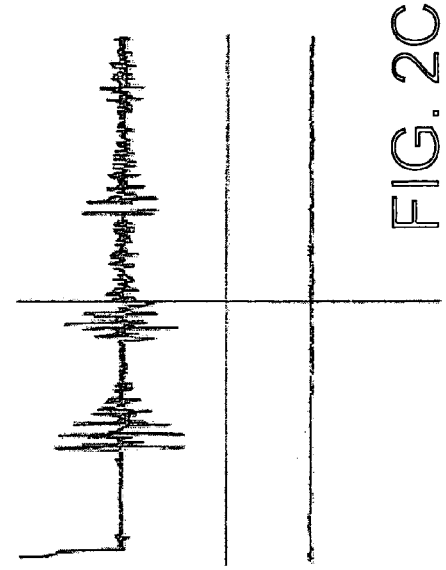
FIGS. 2A, 2B, 2C and 2D illustrate the involved signals.

The following figures show a few examples of signals obtained with the invention through a wetting liquid, the upper trace illustrating the emitted signal and the lower trace the received signal. On FIG. 2A, the target 2 was removed; in the case of FIG. 2B, the target was set up in the wet state; in the case of FIG. 2C, it was set up but not wetted; finally FIG. 2D illustrates an intermediate (partial) wetting of the target 3. Total or partial absence of wetting was reproduced by simulation, by covering the target 2 with an adhesive sheet under which gas was occluded.

The thickness of the target 2 is selected in order to provide maximum transparence and more specifically, it is equal to the half-wavelength of the applied ultrasound. FIG. 2A shows liquid which produces moderate damping of the waves with the appearance of a large receiver signal (462 millivolts at the origin).

Each of the signals also comprises, after the first wave train which represents the provided pulse, successive echoes produced by multiple reflections at the ends of the waveguide 5 or 6.

Figure 2B:
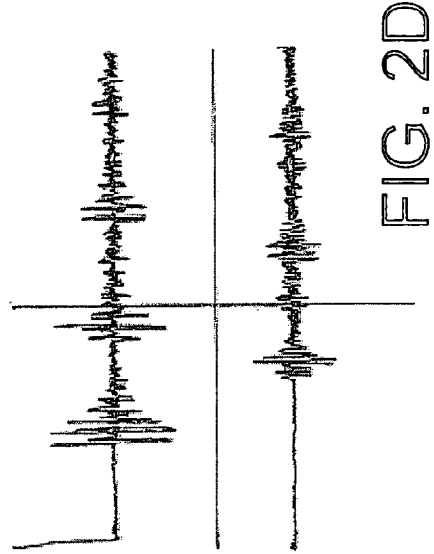

FIG. 2B shows the influence of the damping by the target 2, with only a subsisting 70 millivolt signal. It is also noted that the signal measured on the side of the emitting waveguide 5 comprises echoes from reflections of the waves on target 2.

Figure 2C:
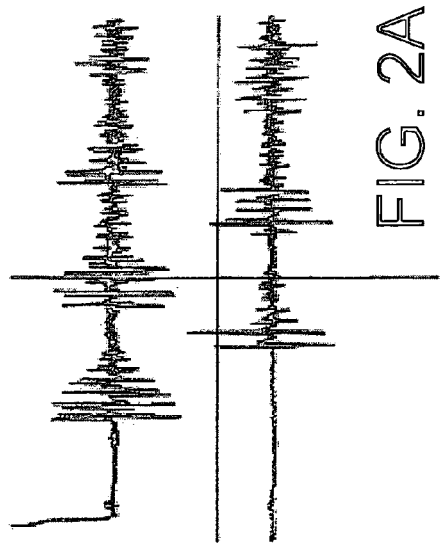
Figure 2D:
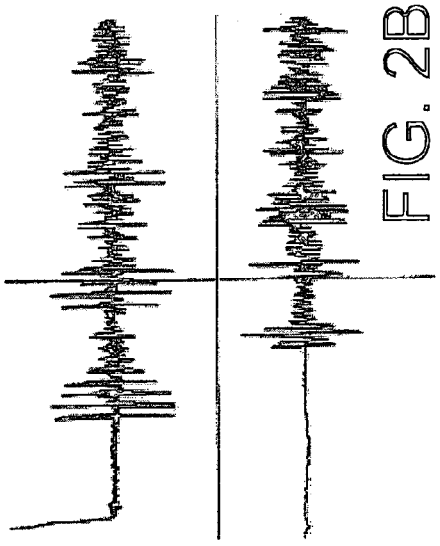

FIG. 2C shows the nearly complete disappearance of the received signal, the emitted energy then being absorbed on the surfaces of the target 2. Finally, the results obtained in FIG. 2D are intermediate with a value at the origin of 40 millivolts.

Hence, the wetting level of the target 2 appears as being proportional to the intensity of the signal which was able to pass through the target 2, of course depending on the intensity of the emitted signal. The intensity at the origin of the received signal is what should be considered.

Certain changes in the design completely discussed above will now be presented more succinctly. It is thus seen in FIG.

Figure 3A:
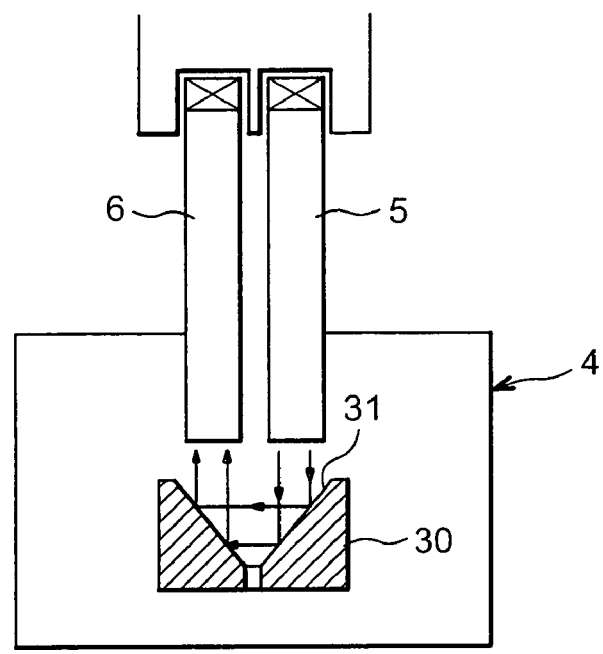
FIGS. 3A and 3B, 4, 5 and 6A, 6B and 6C illustrate other embodiments of the invention.
Figure 3B:
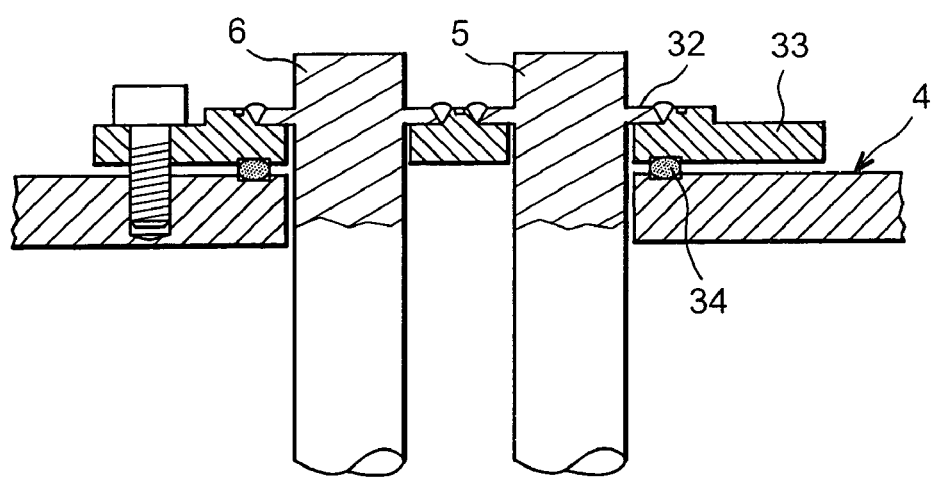

3A, that the waveguides 5 and 6 may be positioned side by side if the target referenced here by 30, is of an appropriate shape, for example a concave shape, and sends back the waves issued from the first waveguide 5 towards the second one (6) after having undergone two reflections in a notch 31. As shown in FIG. 3B, a sealed assembly of the waveguides 5 and 6 through the wall of the capacity 4 is achieved by soldering said guides, at the location of a flange 32, to a bracket 33 blocking an aperture of the capacity wall 4. Waveguides 5 and 6 pass through respective apertures of the bracket 33. A seal gasket 34 is tightly fitted between the capacity 4 and the bracket 33.

Figure 4:
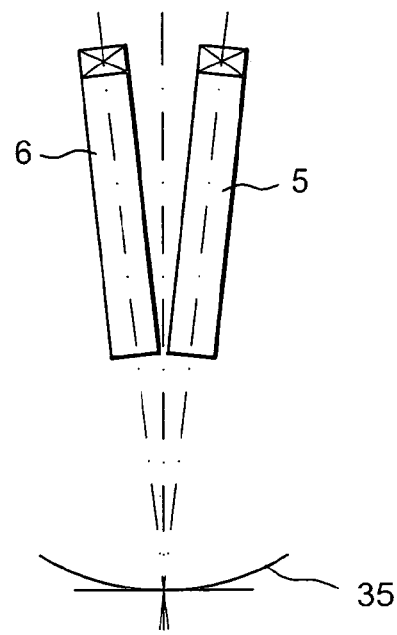
Figure 5:
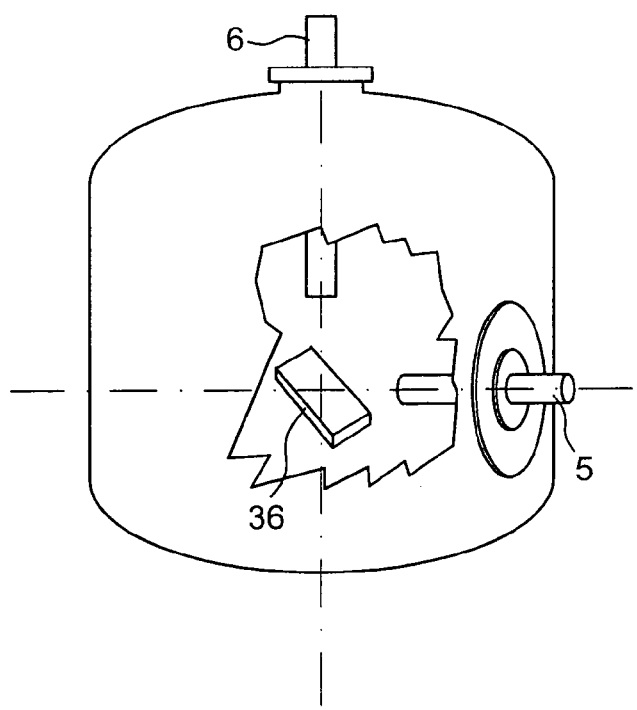

In the embodiment of FIG. 4, waveguides 5 and 6 are no longer parallel but convergent, the target 35 being now concave and only one wave reflection is produced on it. In FIG. 5, both waveguides 5 and 6 are positioned at a right angle, a reflection being produced on a target 36 which is now of a planar shape.

Figure 6A:
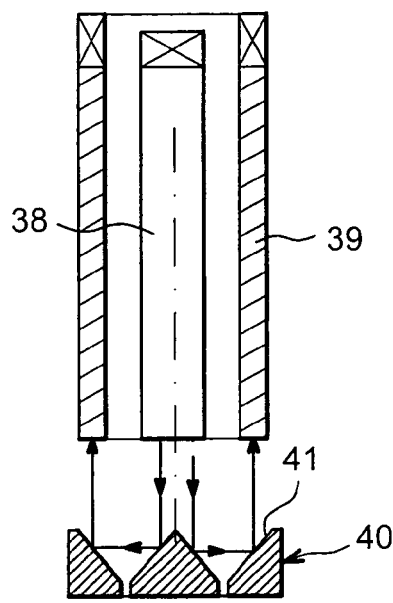
Figure 6B:
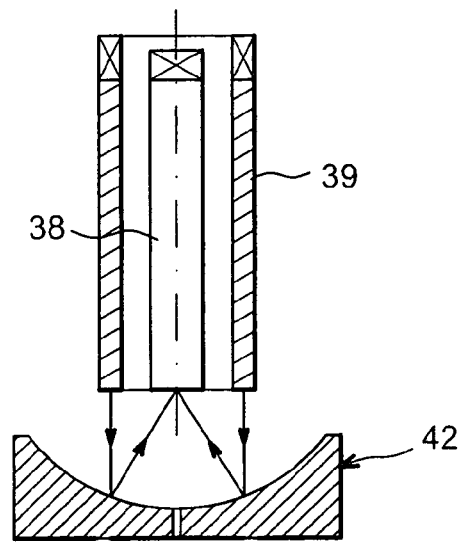

FIGS. 6A and 6B illustrate further embodiments of another design, wherein similar waveguides 5 and 6 are replaced with concentric waveguides, including an interior waveguide 38 like the previous ones (cylindrical) and an external tubular waveguide 39. In the embodiment of FIG. 6A, the interior waveguide is the emitter and waves undergo double reflection on a target 40 provided with a circular notch 41 having a triangular section as in FIG. 3A. However, in the embodiment of FIG. 6B, the external waveguide 39 is the emitter and the waves are reflected towards the entrance of the interior waveguide 38 after having undergone a reflection on a target 42 provided with a rounded imprint like the previous target 35.

Figure 6C:
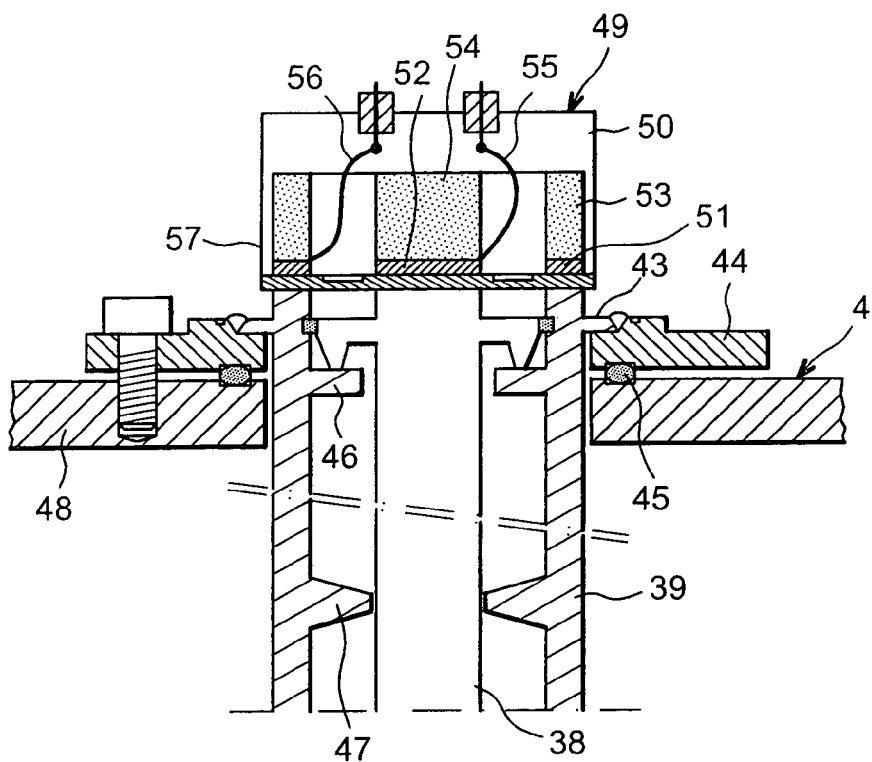

The embodiment of the rear of the device may be that of FIG. 6C, the external waveguide 39 comprising a flange 43 soldered to a bracket 44 screwed to the wall of the capacity 4 and tightly encircling a gasket 45 in the perimeter of the tubular portion dedicated to wave conduction; the external waveguide 39 further comprises an internal flange 46 supporting the interior waveguide 38 and a flange 47 for centering the same interior waveguide 38 is located under the previous one. A supporting ring 48 of the interior waveguide 38 is fitted onto the internal flange 46. A unique transducer 49 is fitted. It has a double function, i.e., it comprises a unique core 50 under which emitting and receiving piezoelectric components, 51 and 52, are deposited. Dampers 53 and 54 are housed behind the piezoelectric components 51 and 52 in the cavities of the core 50. Electrical conductors 55 and 56 connect the piezoelectric components to portions for signal generation and measurement, not shown. Finally, a front blade 57 covers components 51 and 52 and provides the connection with waveguides 38 and 39.

The latter embodiments are all designed for interpreting signals in a reflection mode, which differs from that of the transmission mode of the embodiment of FIG. 1. Here, no signal returns to the receiver in the absence of the target. In the presence of the target, the receiving signal is always present, but has a variable phase lag relatively to the emitted signal depending on the wetting level. When wetting is complete, this phase lag is zero, whereas the phase lag is maximum in the absence of wetting. A detailed time analysis of the signals should therefore be undertaken here.

Generally, it is important that the waveguides withstand the heat from the liquid if the latter is a molten metal. They may be in metal, for example, or may consist of a casing containing another liquid. It is also important that the liquid bathing the target, wets them perfectly which may sometimes be ensured by coating them with an appropriate body, which does not have any other function but ensuring this wetting.

The invention claimed is:

1. A device for determining the wetting of a wall of an object (2) by a liquid, comprising an enclosure (4) for enclosing a defined volume of said liquid; with said object (2) being immersed in the liquid within the enclosure; an emitter and a receiver (15, 16) of ultrasonic waves, and two waveguides (5, 6) extending within the enclosure with the emitter and receiver being respectively mounted on ends of the waveguides external of the enclosure and with the object (2) being placed between the waveguides and having a thickness selected for favoring the passing of waves from the emitter through the object.

2. A device for determining the wetting of a wall of a object by a liquid, comprising: an enclosure (4) for enclosing a defined volume of said liquid; with said object (2) being immersed in the liquid within the enclosure; an emitter and a receiver of ultrasonic waves; and two waveguides passing through the capacity, located side-by-side within the enclosure with the emitter and the receiver being respectively mounted on ends of the waveguides external of the enclosure and with the object (2) being placed in front of the wave guides, the object having a front surface with a geometry selected for favoring reflections of the waves between the waveguides.

3. The device according to claim 1, further comprising heating means for heating the liquid within the enclosure and cooling means located external of the enclosure for cooling the waveguides.

4. The device according to claim 2, further comprising heating means for heating the liquid within the enclosure and cooling means located external of the enclosure for cooling the waveguides.

5. The device according to claim 3, characterized in that the cooling means consists of a case surrounding each of the waveguides between the enclosure and either the emitter or the receiver.

6. The device according to claim 4, characterized in that the cooling means consists of a case surrounding each of the waveguides between the enclosure and either the emitter or the receiver.

7. The device according to claim 1, characterized in that the waveguide is covered with a coating which favors wetting of the liquid in the enclosure.

8. The device according to claim 2, characterized in that the waveguide is covered with a coating which favors wetting of the liquid in the enclosure.

9. The device according to claim 3, characterized in that the waveguide is covered with a coating which favors wetting of the liquid in the enclosure.

10. The device according to claim 4, characterized in that the waveguide is covered with a coating which favors wetting of the liquid in the enclosure.

11. The device according to claim 1, wherein the device further comprises a sealing for the enclosure and a heat insulation system around the waveguides.

12. The device according to claim 2, wherein the device further comprises a sealing for the enclosure and a heat insulation system around the waveguides.

13. The device according to claim 3, wherein the device further comprises a sealing for the enclosure and a heat insulation system around the waveguides.

14. The device according to claim 5, wherein the device further comprises a sealing for the enclosure and a heat insulation system around the waveguides.

15. The device according to claim 5, characterized in that the sealing system comprises a flange positioned around a section of the waveguides and joined to a bracket or a sleeve connected to the enclosure; and the heat insulation system comprises a sleeve or insulating bellows extending between the flange and the cooling case.

16. The device according to claim 7, characterized in that the sealing system comprises a flange positioned around a section of the waveguides and joined to a bracket or a sleeve connected to the enclosure; and the heat insulation system comprises a sleeve or insulating bellows extending between the flange and the cooling case.

17. The device according to claim 11, characterized in that the sealing system comprises a flange positioned around a section of the waveguides and joined to a bracket or a sleeve connected to the enclosure; and the heat insulation system comprises a sleeve or insulating bellows extending between the flange and the cooling case.

* * * * *